(12) United States Patent
Schölly

(10) Patent No.: US 7,404,794 B2
(45) Date of Patent: Jul. 29, 2008

(54) MICROENDOSCOPE

(75) Inventor: Werner Schölly, Denzlingen (DE)

(73) Assignee: Scholly Fiberoptic GmbH, Denzlingen (DE)

( * ) Notice: Subject to any disclaimer, the term of this patent is extended or adjusted under 35 U.S.C. 154(b) by 460 days.

(21) Appl. No.: 10/515,562

(22) PCT Filed: May 20, 2003

(86) PCT No.: PCT/EP03/05274

§ 371 (c)(1),
(2), (4) Date: Nov. 22, 2004

(87) PCT Pub. No.: WO03/098315

PCT Pub. Date: Nov. 27, 2003

(65) Prior Publication Data

US 2005/0261554 A1    Nov. 24, 2005

(30) Foreign Application Priority Data

May 22, 2002    (DE) ................. 102 22 505

(51) Int. Cl.
*A61B 1/00*    (2006.01)
(52) U.S. Cl. .............. 600/182; 600/160; 600/136; 600/112; 385/117
(58) Field of Classification Search ........... 600/109, 600/112, 131, 136, 138, 160, 182; 385/116, 385/117
See application file for complete search history.

(56) References Cited

U.S. PATENT DOCUMENTS

| | | | |
|---|---|---|---|
| 4,269,485 A | | 5/1981 | Yamashita et al. |
| 4,628,207 A | | 12/1986 | Elfert et al. |
| 4,721,359 A | * | 1/1988 | Nishioka et al. ............ 385/117 |
| 4,772,093 A | * | 9/1988 | Abele et al. ................ 385/119 |
| 4,854,302 A | * | 8/1989 | Allred, III ................... 600/109 |
| 5,188,093 A | * | 2/1993 | Lafferty et al. ............. 600/109 |
| 5,423,312 A | * | 6/1995 | Siegmund et al. .......... 600/109 |
| 5,665,051 A | * | 9/1997 | Quick et al. ................ 600/161 |
| 5,751,869 A | * | 5/1998 | Li et al. ..................... 385/116 |
| 6,960,161 B2 | * | 11/2005 | Amling et al. ............. 600/112 |

FOREIGN PATENT DOCUMENTS

| | | |
|---|---|---|
| DE | 40 09 438 | 9/1991 |
| DE | 198 59 155 | 7/2000 |
| DE | 100 33 142 | 1/2001 |
| DE | 101 55 921 | 5/2002 |
| EP | 0 609 093 | 8/1994 |
| WO | 01/63334 | 8/2001 |

* cited by examiner

*Primary Examiner*—John P. Leubecker
(74) *Attorney, Agent, or Firm*—Volpe And Koenig, P.C.

(57) ABSTRACT

A microendoscope with a distal probe tip which has, in particular, a diameter of up to approximately 1 mm is provided and inside of which an optical subassembly at least provided with a micro-objective and with an image transmitting element is accommodated. An image transmitting system is connected to the optical subassembly. An image-enlarging coupling element is provided between the optical subassembly of the probe tip and the image transmitting system connected thereto. The image transmitting system connected to the coupling element has a larger active diameter than the optical subassembly that is provided with the distal objective. As a result, the distal probe tip on a handgrip has the necessary small working diameter over the entire working length, and at the beginning or inside the handgrip, the optical coupling element is coupled to an image guide or to an image transmitting system or the like having a higher pixel count and thus a larger active diameter and, therefore, a larger outside diameter.

2 Claims, 1 Drawing Sheet

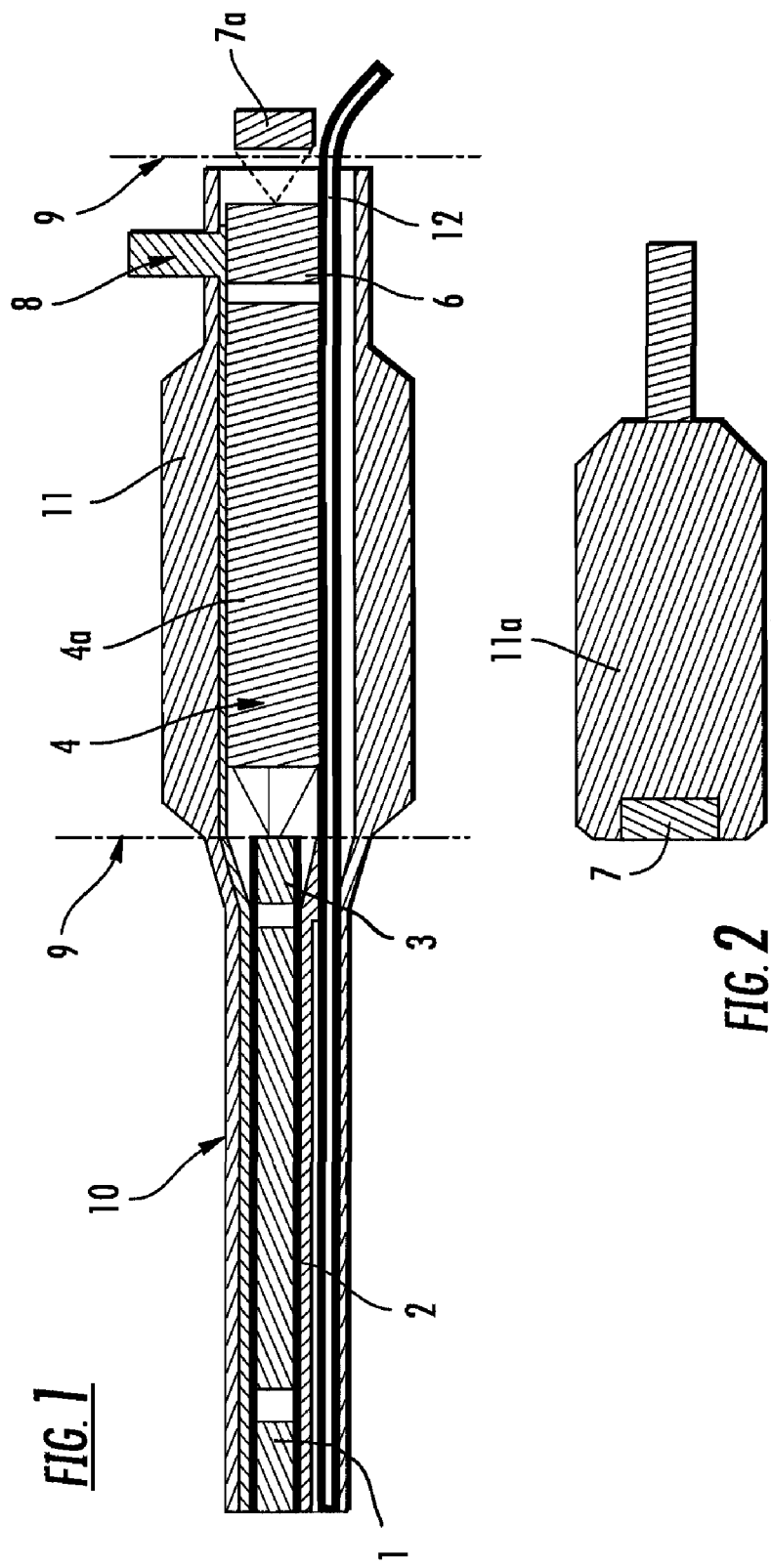

MICROENDOSCOPE

BACKGROUND

The invention relates to a microendoscope with a distal probe tip, which has, in particular, a diameter of up to approximately 1 mm and which houses an optical subassembly at least provided with a micro-objective and an image-transmitting element, with an image-transmitting system being connected to the optical subassembly.

In microendoscopy, for working diameters below 1 mm, flexible endoscopes are known, which have close to the distal end a lightweight handle, whose rigid tip can extend, for example, over a length of 30-120 mm. The microendoscope tip generally has the following structure:

In the center at the distal end there is a micro-objective, formed from one or more micro-lenses, e.g., with an outer diameter of 0.5 mm. This distal micro-objective is usually placed directly on a subsequent image guide with the same active diameter. At the proximal end, the pixel-structured image transmitted by the image guide is prepared by an objective for visual observation or for projection on a video-camera array.

Optical fibers, which are fastened mechanically close to the proximal end and which are connected to a light source via a connecting light guide, are arranged around the distal micro-objective and the image guide along the probe length for illuminating the image field. In the region of the distal tip, micro-objectives, image guides, and optical fibers are installed in a rigid or semi-flexible tube, which forms a holder and guide for these components.

The light-transmitting and image-transmitting elements are usually fastened in a flexible protective sleeve from the handle outwards to the proximal end. For certain applications, an empty channel, represented, for example, by a micro-lumen sleeve or a metal tube, can also be integrated into the probe.

Many microendoscopic applications in medical technology and for industrial applications require small working diameters starting at 0.15 up to about 1 mm. These working diameters permit only about 3000 pixels for the image guide due to space requirements; however, the applications demand higher resolutions with more than at least 10,000 pixels (e.g., 20,000, 30,000, 50,000). In addition, the handle of the microendoscopic probe and the probe feed line should be configured as lightweight as possible, which requires the image-transmitting system to have a flexible image-guiding system to the endoscopic camera (for video observation). Image guides with pixel counts greater than 3000 do not allow distal probe tips with working diameters of less than 0.5 mm for the structure described above.

SUMMARY

The objective of the present invention is to permit the realization of microendoscopic probe tips with a very small working diameter of, for example, <0.5 mm, lightweight handles and probe feed lines, which simultaneously allow achievement of a significantly higher resolution than before.

To achieve this object, it is proposed that an image-enlarging coupling element be provided between the optical subassembly of the probe tip and the connected image-transmitting system, and that the image-transmitting system connected to the coupling element have a greater active diameter than the optical subassembly with the distal objective.

The invention is thus based on the principle of equipping the distal probe tip at the handle with an optical subassembly (micro-lens subassembly), which enables the necessary small working diameter, over the entire working length and of using an optical coupling element to couple at the beginning or in the interior of the handle to an image guide with higher pixel count and thus greater active diameter and therefore also outer diameter.

The miniaturized probe tip can also be configured so that it is removable and thus can be sterilized using steam for medical applications. In another configuration, instead of the image guide, a micro-camera head can also be integrated in the handle. The coupling optics of the distal probe tip forms an image on this camera head.

Typical handles for microendoscopic probes can have outer diameters of about 8-10 mm for a length of >50 mm. Miniature CCD imagers with $\frac{1}{10}$" image diagonals and 250,000 pixels can be integrated in this volume and thus represent a high resolution in the image field of the probe.

Additional embodiments of the invention are given in the other subordinate claims.

BRIEF DESCRIPTION OF THE DRAWINGS

In the following, the invention is explained in more detail with its essential features with reference to the drawings.

Shown are:

FIG. 1 is a longitudinal section of a microendoscope and

FIG. 2 is a sectional representation of an alternate handle part with CCD image converter.

DETAILED DESCRIPTION OF THE PREFERRED EMBODIMENTS

The structure according to the invention from FIG. 1 is as follows:

The distal objective 1, which can be formed of one or more micro-optical components, for example, a graded index lens, is connected before an image-transmitting rod-lens system 2 made from one or more elements, preferably a graded rod. The optical coupling element 3 images the image transmitted by 1 and 2 full-format on the significantly greater active image-field diameter of the image guide 4a than the image-transmitting system 4 or of the micro-CCD image converter 7 according to FIG. 2. The image-transmitting system 4 has a fiber-optic image guide 4a with high pixel count, preferably with more than 10,000 pixels. For the use of the image guide 4a, at the proximal end another objective 6 is provided, which forms an image of approximately full format on the image-field size of the CCD image converter 7a of an endoscope camera. An empty channel 12 for washing and/or applicators such as laser fibers is also integrated into the microendoscope.

In the probe tip region, concentric optical fibers are arranged for illuminating the image field, which can be realized at an optional separating point 9, preferably as ring light or as a single-point or multiple-point transfer system. The rear light-guide end is designated with 8.

In the configuration with the separating point, the element 3 can be integrated either in the probe tip 10 or in the handle part 11, 11a. The removable probe tips can be realized with different imaging angles and viewing directions.

The invention claimed is:

1. Microendoscope comprising a distal probe tip, which has a diameter of up to approximately 1 mm, wherein in the probe tip over the working length is an optical subassembly at least with a micro-objective and a connected micro-lens system as an image transmitting element, the probe tip with the optical subassembly is removably connected to a probe handle, and in an area of the probe handle the optical subassembly of the probe tip is connected to an image-transmitting system which has a greater active diameter than the optical subassembly of the probe tip, and includes a fiber-optic image guide with a pixel count of more than 10,000 pixels, and between the optical subassembly of the probe tip and the image guide connected thereto, an image enlarging coupling element is provided.

2. Microendoscope of claim 1, wherein the microendoscope includes an empty channel for at least one of rinsing or applicators.

* * * * *